(12) United States Patent
Arhancet et al.

(10) Patent No.: US 10,329,518 B2
(45) Date of Patent: *Jun. 25, 2019

(54) ANIONIC SURFACTANTS

(71) Applicant: Novus International Inc., St. Charles, MO (US)

(72) Inventors: Graciela B. Arhancet, St. Charles, MO (US); Scott A. Long, St. Charles, MO (US); Brian Grady, Norman, OK (US); Jeff Harwell, Norman, OK (US); Guangzhe Yu, Norman, OK (US)

(73) Assignees: Board of Regents of the University of Oklahoma, Norman, OK (US); Novus International, Inc., St. Charles, MO (US)

( * ) Notice: Subject to any disclaimer, the term of this patent is extended or adjusted under 35 U.S.C. 154(b) by 257 days.

This patent is subject to a terminal disclaimer.

(21) Appl. No.: 15/197,010

(22) Filed: Jun. 29, 2016

(65) Prior Publication Data

US 2017/0002295 A1 Jan. 5, 2017

Related U.S. Application Data

(60) Provisional application No. 62/187,858, filed on Jul. 2, 2015.

(51) Int. Cl.
| | | |
|---|---|---|
| C11D 1/06 | (2006.01) |
| C11D 1/00 | (2006.01) |
| C07C 323/52 | (2006.01) |
| C07C 319/20 | (2006.01) |
| C07C 315/04 | (2006.01) |
| C07C 315/02 | (2006.01) |
| C07C 317/46 | (2006.01) |

(52) U.S. Cl.
CPC .............. *C11D 1/06* (2013.01); *C07C 315/02* (2013.01); *C07C 315/04* (2013.01); *C07C 317/46* (2013.01); *C07C 319/20* (2013.01); *C07C 323/52* (2013.01); *C11D 1/002* (2013.01)

(58) Field of Classification Search
CPC ... C07C 317/46; C07C 323/52; C07C 315/02; C07C 315/04; C11D 1/06; C11D 1/002
See application file for complete search history.

(56) References Cited

U.S. PATENT DOCUMENTS

| | | |
|---|---|---|
| 4,464,292 A | 8/1984 | Lengyel |
| 5,348,978 A | 9/1994 | Baxter |
| 6,221,637 B1 | 4/2001 | Hida |
| 6,310,095 B1 | 10/2001 | Sebti |
| 6,949,498 B2 | 9/2005 | Murphy |
| 9,801,845 B2 * | 10/2017 | Arhancet ............... A23K 10/18 |
| 2002/0193596 A1 | 12/2002 | Sebti |
| 2004/0175434 A1 * | 9/2004 | Schasteen ............... A01N 37/36 424/659 |
| 2013/0178540 A1 | 7/2013 | Grady |
| 2013/0209392 A1 | 8/2013 | Arhancet |

FOREIGN PATENT DOCUMENTS

| | | |
|---|---|---|
| EP | 0572271 A2 | 12/1993 |
| EP | 2082739 A1 | 7/2009 |
| JP | 06316557 | 11/1994 |
| JP | H06 316557 A | 11/1994 |
| WO | 9200276 A2 | 1/1992 |
| WO | 2003106615 | 12/2003 |
| WO | 2006019149 | 2/2006 |
| WO | 2009137465 | 11/2009 |
| WO | 2013150058 A1 | 10/2013 |
| WO | 2015100225 | 7/2015 |
| WO | 2017004161 A1 | 1/2017 |

OTHER PUBLICATIONS

Zaragoza Dorwald, Side Reactions in Organic Synthesis, 2005, Wiley-VCH Verlag GmbH & Co. KGaA, Weinheim, Preface. p. IX. (Year: 2005).*

International Search Report and Written Opinion dated Mar. 26, 2015 from related international application No. PCT/US14/71860, 9 pgs.

Acevedo et al., Molecular Weight of Petroleum Asphaltenes: A Comparison between Mass Spectrometry and Vapor Pressure Osmometry, Energy & Fuels, 2005, 19(4): 1548-1560.

Blanco et al., A comparative study of the physicochemical properties of perfluorinated and hydrogenated amphiphiles, Journal of Colloid and Interface Science, 2005, 288: 247-260.

(Continued)

*Primary Examiner* — Paul A Zucker
(74) *Attorney, Agent, or Firm* — Polsinelli PC

(57) ABSTRACT

Monomeric and oligomeric compounds of Formula (I) comprising hydrophobic alkyl or alkenyl ester moieties and hydrophilic carboxylate moieties:

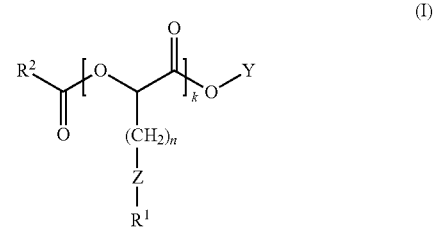

(I)

wherein $R^1$ is $C_1$-$C_6$ alkyl, $R^2$ is $C_{10}$-$C_{30}$ alkyl or $C_8$-$C_{30}$ alkenyl, Y is a cation, Z is a sulfur-containing moiety, and n and k are integers as defined herein. The compounds of Formula (I) have surfactant properties. Also provided are compositions comprising the compounds of Formula (I), and methods of using the compounds or compositions for cleaning purposes.

14 Claims, No Drawings

(56) References Cited

OTHER PUBLICATIONS

Buchwald et al., Quantitative structure-metabolism relationships: steric and nonsteric effects in the enzymatic hydrolysis of noncongener carboxylic esters, Journal of Medicinal Chemistry (1999), 42(25), 5160-5168.

Dahanayake et al., Relationship of structure to properties of surfactants. 13. Surface and thermodynamic properties of some oxyethylenated sulfates and sulfonates, Journal of Physical Chemistry, 1986, 90(11): 2413-2418.

Ge et al., Crystallographic studies on the binding of selectively deuterated LLD- and LLL-substrate epimers by isopenicillin N synthase. Biochemical and Biophysical Research Communications, (2010), 398(4), 659-664.

Glukhareva at al., Krafft points of some mixtures based on individual sodium soaps, Colloid Journal of the Russian Academy of Sciences, 1995, 57: 253-255.

Guzman et al., Molecular Weight Determination of Asphaltenes from Colombian Crudes by Size Exclusion Chromatography (SEC) and Vapor Pressure Osmometry (VPO), Petroleum Science and Technology, 2009, 27(8): 801-816.

Jackson et al., Mixtures of Nonionic Surfactants made from Renewable Resources with Alkyl Sulfates and Sodium n-Alkanecarboxylates: Comparison of Mixing Behavior using Rubingh's Treatment , Journal of Surfactants and Detergents, 2013, 16(6): 893-902.

Moore et al., Pharmacological effects of introducing a double bond into a binding site of oxytocin. Analogues with L-3,4-dehydroproline in position 7, Journal of Medicinal Chemistry, 1977, 20(4), 495-500.

Onisko et al., Metabolism of cycloate in radish leaf: metabolite identification by packed capillary flow fast atom bombardment tandem mass spectrometry, Biological Mass Spectrometry, 1994, 23(10), 626-36.

Onisko et al., Identification of fonofos metabolites in Latuca sativa, Beta vulgaris, and Triticum aestivum by packed capillary flow fast atom bombardment tandem mass spectrometry, Journal of Agricultural and Food Chemistry, 2002, 50(7), 1922-1928.

Stellner et al., Hardness tolerance of anionic surfactant solutions. 1. Anionic surfactant with added monovalent electrolyte, Langmuir, 1989, 5(1): 70-77.

International Search Report and Written Opinion dated Sep. 19, 2016 from related international Application No. PCT/US16/40025, 8 pgs.

Annett et al.,. 2002. Necrotic enteritis: effect of barley, wheat and corn diets on proliferation of Clostridium perfringens type A. Avian Pathology, 2002, 31: 599-602.

Lensing et al., Efficacy of a lactylate on production performance and intestinal health of broilers during subclinical Clostridium Perfringens infection, Poultry Science, 2010, 89:2401-2409.

Extended European Search Report dated Dec. 21, 2018 in related Application No. 16818655.9, 7 pp.

Huthmacher, Miscellaneous Biopolymers and Biodegradation of Synthetic Polymers, Biopolymers, 2003, vol. 9, Chapter 4, 9 pp.

\* cited by examiner

ANIONIC SURFACTANTS

CROSS-REFERENCE TO RELATED APPLICATIONS

This application claims the priority of U.S. provisional Application No. 62/187,858, filed Jul. 2, 2015, which is hereby incorporated by reference in its entirety.

FIELD OF THE INVENTION

The present disclosure generally relates to surfactants. In particular, it relates to sulfur-containing compounds comprising hydrophobic ester moieties and carboxylate moieties, wherein the compounds have surfactant properties.

BACKGROUND OF THE INVENTION

Anionic surfactants are essential in various applications, especially detergency. Anionic surfactants with carboxylic acid moieties have been used for thousands of years; soap was first made from the hydrolysis of naturally-occurring oils/fats. Fatty acid surfactants have an excellent combination of properties including low CMC, low surface tension at the CMC, good foaming characteristics and mildness when applied to skin. However, the 20$^{th}$ century has seen the use of these surfactants relative to other anionic surfactants decrease significantly. The most significant disadvantage of carboxylate surfactants as opposed to other anionic surfactants is their propensity to precipitate when divalent cations, e.g., calcium and magnesium, are present; in other words carboxylate surfactants have inferior hardness tolerance. Thus, there is a need for new carboxylate anionic detergents with high solubility and good hardness tolerance.

SUMMARY OF THE INVENTION

Among the various aspects of the present disclosure is the provision of a compound of Formula (I):

(I)

wherein:
- $R^1$ is alkyl, substituted alkyl, alkenyl, substituted alkenyl, aryl, or substituted aryl;
- $R^2$ is alkyl, substituted alkyl, alkenyl, or substituted alkenyl, provided that when Z is sulfur and k is 1, the alkyl or substituted alkyl has at least 10 carbon atoms in the principal chain;
- Y is a cation chosen from hydrogen, ammonium, alkali metal, alkaline earth metal, or transition metal;
- Z at each occurrence is sulfur, sulfoxide, or sulfone;
- k is an integer of 1 or greater; and
- n is an integer of 1 or greater.

Another aspect of the present disclosure encompasses a method for cleaning an article. The process comprises contacting the article with a composition comprising at least one compound of Formula (Ib):

(Ib)

wherein:
- $R^1$ is alkyl, substituted alkyl, alkenyl, substituted alkenyl, aryl, or substituted aryl;
- $R^2$ is alkyl, substituted alkyl, alkenyl, or substituted alkenyl;
- M is a cation chosen from ammonium, alkali metal, alkaline earth metal, or transition metal;
- Z at each occurrence is sulfur, sulfoxide, or sulfone;
- k in an integer of 1 or greater; and
- n is an integer of 1 or greater.

A further aspect of the present disclosure provides a process for preparing compounds of Formula (Ib). The process comprises (a) contacting compounds of Formula (II) with an acyl halide, $R^2C(O)X$, to form compounds of Formula (Ia); and (b) contacting the compounds of Formula (Ia) with a salt, MA, to form compounds of Formula (Ib) according to the following reaction scheme:

(II)  →$R^2C(O)X$→  (Ia)

↓ MA (Ib)

wherein:
- $R^1$ is alkyl, substituted alkyl, alkenyl, substituted alkenyl, aryl, or substituted aryl;
- $R^2$ is alkyl, substituted alkyl, alkenyl, or substituted alkenyl;
- A is an anion;
- M is a cation chosen from ammonium, alkali metal, alkaline earth metal, or transition metal;
- X is a halide ion;
- Z at each occurrence is sulfur, sulfoxide, or sulfone;
- k is an integer of 1 or greater; and
- n is an integer of 1 or greater.

Yet another aspect of the present disclosure provides a process for preparing compounds of Formula (Ia). The process comprises (a) contacting compounds of Formula (IIa) with an acyl halide, $R^2C(O)X$, to form compounds of Formula (Ic); and (b) contacting the compounds of Formula (Ic) with an oxidizing agent to form compounds of Formula (Ia) according to the following reaction scheme:

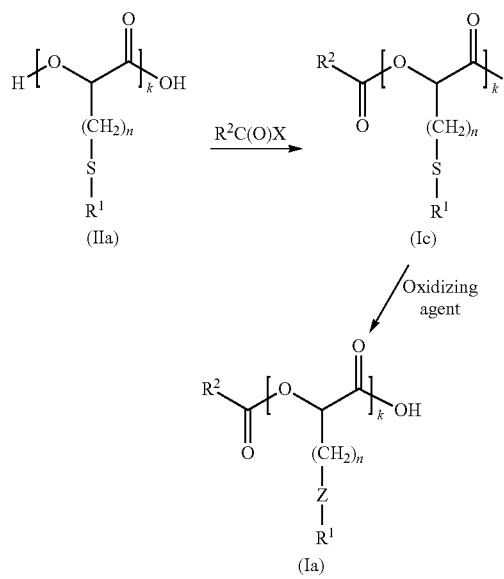

wherein:

$R^1$ is alkyl, substituted alkyl, alkenyl, substituted alkenyl, aryl, or substituted aryl;

$R^2$ is alkyl, substituted alkyl, alkenyl, or substituted alkenyl;

X is a halide ion;

Z is sulfoxide or sulfone;

k is an integer of 1 or greater; and n is an integer of 1 or greater.

Other features and iterations of the invention are described in more detail below.

DETAILED DESCRIPTION OF THE INVENTION

The present disclosure provides anionic surfactants, compositions comprising the anionic surfactants, methods of using the anionic surfactants for a variety of applications, and processes for preparing the anionic surfactants. The anionic surfactants disclosed herein are branched carboxylates comprising a hydrophobic ester moiety and a sulfur-containing moiety. The sulfur-containing carboxylate surfactants exhibit critical micelle concentrations and are soluble in water over a wide range of concentrations and temperatures. Moreover, water solutions comprising the sulfur-containing carboxylate surfactants have low surface tensions and excellent tolerance to divalent cations.

(I) Compounds of Formula (I)

(a) Structures

One aspect of the present disclosure provides a compound of Formula (I) or a mixture of compounds having Formula (I):

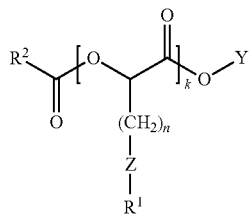

wherein:

$R^1$ is hydrocarbyl or substituted hydrocarbyl;

$R^2$ is alkyl, substituted alkyl, alkenyl, or substituted alkenyl, provided that when Z is sulfur and k is 1, the alkyl or substituted alkyl has at least 10 carbon atoms in the principal chain;

Y is a cation chosen from hydrogen, ammonium, alkali metal, alkaline earth metal, or transition metal;

Z at each occurrence is sulfur, sulfoxide, or sulfone;

k is an integer of 1 or greater; and n is an integer of 1 or greater.

In some embodiments, Y is hydrogen, and the compound of Formula (I) is a carboxylic acid of Formula (Ia):

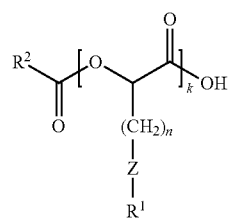

wherein $R^1$, $R^2$, Z, k, and n are as defined above.

In other embodiments, Y is a cation other than hydrogen and the compound of Formula (I) is a carboxylate of Formula (Ib):

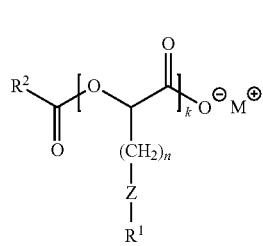

wherein $R^1$, $R^2$, Z, k, and n are as defined above, and M is a cation chosen from ammonium, an alkali metal, an alkaline earth metal, or a transition metal. Suitable metals include sodium, potassium, lithium, cesium, magnesium, calcium, manganese, cobalt, nickel, copper, zinc, and iron. The ratio of the anionic compound to the metal may range from about 1:1 to about 3:1. In specific embodiments, the cation may be sodium or potassium.

In various embodiments, $R^1$ may be unsubstituted or substituted alkyl, alkenyl, or aryl. In some embodiments, $R^1$ may be $C_1$ to $C_6$ alkyl or $C_1$ to $C_6$ alkenyl, wherein alkyl and alkenyl may be linear, branched, or cyclic. In certain embodiments, $R^1$ may be methyl, ethyl, propyl, isopropyl, butyl, tert-butyl, hexyl, cyclohexyl, and the like. In specific embodiments, $R^1$ may be methyl.

In certain embodiments, $R^2$ may be $C_{10}$ to $C_{30}$ alkyl, substituted $C_{10}$ to $C_{30}$ alkyl, $C_8$ to $C_{30}$ alkenyl, or substituted $C_8$ to $C_{30}$ alkenyl. The alkyl and alkenyl groups may be linear, branched, or cyclic, and the alkenyl groups may contain from one to six carbon-carbon double bonds. In some embodiments, $R^2$ may be $C_{10}$ to $C_{24}$ alkyl or $C_{10}$ to $C_{24}$ alkenyl. In specific embodiments, $R^2$ may be $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{24}$ alkyl or alkenyl.

In embodiments, in which k is greater than 1, Z may vary in each repeated unit. In other embodiments, Z is the same in each repeat unit. In specific embodiments, Z may be sulfur or sulfoxide.

In various embodiments, k may range from 1 to several thousand. In some embodiments, k may range from 1 to 500, from 1 to 100, from 1 to 50, from 1 to 20, from 1 to 10, from 1 to 9, from 1 to 8, from 1 to 7, from 1 to 6, from 1 to 5, from 1 to 4, from 1 to 3, or from 1 to 2. In specific embodiments, k may range from 1 to 10.

In some embodiments, n may be an integer from 1 to 20, from 1 to 10, or from 1 to 6. In certain embodiments, n may be 1, 2, 3, or 4. In specific embodiments, n may be 2.

In exemplary embodiments, Y is hydrogen, sodium, or potassium, $R^1$ is methyl; $R^2$ is $C_{10}$ to $C_{24}$ alkyl, Z is sulfur or sulfoxide, k ranges from 1 to 10, and n is 2.

(b) Stereochemistry

The compounds of Formula (I) disclosed herein generally have at least one chiral center, as denoted with an asterisk in the schematic below

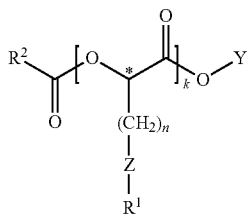

(I)

wherein $R^1$, $R^2$, Y, Z, k, and n are as defined above. The compounds disclosed herein may comprise additional chiral centers.

Each chiral center may have an R or an S configuration. In compounds comprising one chiral carbon, the configuration may be R or S. In compounds comprising two or more chiral carbons, the configuration of each will be independently R or S. For example, in compounds comprising two chiral carbons, the configuration may be RR, RS, SR, or SS, in compounds comprising three chiral carbons, the configuration may be RRR, RRS, RSR, RSS, SRR, SRS, SSR, or SSS, and so forth.

(c) Surfactant Properties of Compounds of Formula (Ib)

Compounds of Formula (Ib) described above have surfactant properties (e.g., see Examples 5-8). For example, compounds of Formula (Ib) have a critical micelle concentration (CMC) in water at 25° C. and atmospheric pressure. For example, the CMC may range from about 0.0001 to about 100 mM in water at 25° C. and atmospheric pressure. In various embodiments, compounds of Formula (Ib) may have a CMC that ranges from about 0.0001 to about 0.0003 mM, from about 0.0003 to about 0.001 mM, from about 0.001 to about 0.003 mM, from about 0.003 to about 0.01 mM, from about 0.01 to about 0.03 mM, from about 0.03 to about 0.1 mM, from about 0.1 to about 0.3 mM, from about 0.3 to about 1 mM, from about 1 to about 3 mM, from about 3 to about 10 mM, from about 10 to about 30 mM, or from about 30 to about 100 mM in water at 25° C. and atmospheric pressure. In specific embodiments, compounds of Formula (Ib) may have a CMC of less than about 2 mM in water at 25° C. and atmospheric pressure.

The compounds of Formula (Ib) are highly soluble in aqueous solutions. In general, the solubility of compounds of Formula (Ib) may range from about 10 mM to greater than about 2,000 mM in water at 25° C. and atmospheric pressure. In various embodiments, the solubility of compounds of Formula (Ib) in water may be at least about 20 mM, at least about 50 mM, at least about 100 mM, at least about 200 mM, at least about 500 mM, at least about 1,000 mM, at least about 2,000 mM, or greater than about 2,000 mM.

In general, the compounds of Formula (Ib) have low surface tensions. Typically, compounds of Formula (Ib) have surface tensions that range from about 15 mN/m to about 60 mN/m at CMC (and at 25° C. and atmospheric pressure). In certain embodiments, compounds of Formula (Ib) may have surface tensions of about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 mN/m at CMC (and at 25° C. and atmospheric pressure).

(II) Compositions Comprising Compounds of Formula (Ib)

Another aspect of the present disclosure encompasses compositions comprising at least one anionic surfactant of Formula (Ib). The compositions further comprise at least one additional agent.

(a) Anionic Surfactant

The compositions disclosed herein comprise at least one anionic surfactant of Formula (Ib):

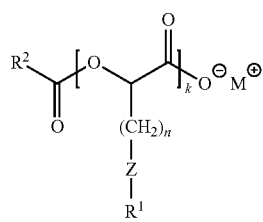

(Ib)

wherein $R^1$, $R^2$, M, Z, k, and n are as defined above in section (I)(a).

The amount of the compound(s) of Formula (Ib) present in the composition can and will vary. In general, the weight fraction of the compounds of Formula (Ib) may range from about 0.1% to about 50% of the composition. In various embodiments, the weight fraction of the compounds of Formula (Ib) may range from about 0.1% to about 1%, from about 1% to about 3%, from about 3% to about 10%, from 10% to about 30%, or from about 30% to about 50% of the composition.

(b) Additional Agents

The detergent compositions disclosed herein also further comprise at least one agent chosen from pH regulating agents, stain-removing enzymes, other types of surfactants, optical brightening agents, bleaching agents, thickening agents, scale inhibitors, chelating agents, water softening agents, foam control agents, dispersants, hydrotropes, linkers, fillers, disintegrants, solvents, skin conditioning agents, preservatives, coloring agents, fragrance agents, or combinations thereof.

In some embodiments, the composition may comprise at least one pH regulating agent. Non-limiting examples of suitable pH regulating agents include organic carboxylic acids (e.g., acetic acid, ascorbic acid, citric acid, formic acid, glycolic acid, gluconic acid, lactic acid, malic acid, maleic acid, propionic acid, succinic acid, tartaric acid, etc.) or salts thereof other acids (e.g., hydrochloric acid, boric acid, nitric acid, phosphoric acid, sulfuric acid, etc.), alkali metal or ammonium carbonates, bicarbonates, hydroxides, phosphates, nitrates, and silicates; organic bases (such as, for example, pyridine, triethylamine (i.e., monoethanol amine), diisopropylethylamine, N methylmorpholine, N,N dimethylaminopyridine); and combinations of any of the above.

In other embodiments, the composition may comprise at least one stain-removing enzyme. Suitable enzymes include but are not limited to proteases, peptidases, subtilisin, mannanases, amylases, carbohydrases, and lipases.

In still other embodiments, the composition may comprise at least one different type of surfactant. For example, the different surfactant may be another class of nonionic surfactant, an anionic surfactant, or a cationic surfactant. Non-limiting examples of suitable nonionic surfactants (including zwitterionic surfactants that have no net charge) include alcohol ethoxylates, alkyl phenol ethoxylates (e.g., nonylphenyl ethoxylate), thiol ethoxylates, fatty acid ethoxylates, glycerol esters, hexitol esters, amine ethoxylates, alkylamide ethoxylates, and imide ethoxylates. Suitable anionic surfactants include, but are not limited to, alkyl sulfates, alkyl ether sulfates, sulfated alkanolamides, glyceride sulfates, dodecyl benzene sulfonates, alkylbenzene sulfonates, alpha olefin sulfonates, and sulfocarboxylic compounds. Exemplary anionic surfactants include sodium dodecylbenzene sulfonate, sodium methyl cocoyl taurate, sodium lauryl sulfate, sodium laureth sulfate, ammonium lauryl sulfate, ammonium laureth sulfate, TEA-lauryl sulfate. Non-limiting examples of suitable cationic surfactants include alkyl amines, quaternary alkyl ammoniums, ester amines, and ether amines. Specific cationic surfactants include cocamidopropyl betaine, lauramidopropyl betaine, In further embodiments, the composition may comprise at least one optical brightener. Optical brighteners (also known as optical brightening agents, fluorescent brightening agents, or fluorescent whitening agents) are dyes that absorb light in the ultraviolet and violet region and reemit light in the blue regions. Non-limiting examples of suitable optical brightening agents include triazine-stilbenes, coumarins, imidazolines, diazoles, triazoles, benzoxazolines, and biphenyl-stilbenes. In one embodiment, the optical brightening agent may be a sulfonated tetrabenzotetraaza porphyrin derivative. In some embodiments, the optical brightening agent may be used in combination with a polyol, such as polyethylene glycol, polypropylene glycol, or polyvinyl alcohol.

In still other embodiments, the composition may comprise at least one bleaching agent. Suitable bleaching agents include without limit hydrogen peroxide, peroxy acid, sodium perborate, sodium percarbonate, sodium hypochlorite, and sodium dichloroisocyanurate.

In some embodiments, the composition may comprise at least one thickening agent (or rheological additive). Suitable thickening agents include but are not limited to cellulosic ethers (such as hydroxycellulose, hydroxypropyl cellulose, hydroxymethylpropyl cellulose, hydroxyethyl cellulose, carboxymethyl cellulose, methylhydroxyethyl cellulose), polyvinylpyrrolidone, poly(vinylpyridine-N-oxide), bentonites, starches, gums, and combinations thereof.

In certain embodiments, the composition may comprise at least one scale inhibitor. Non-limiting examples of suitable scale inhibitors include phosphonates, sodium hexametaphosphate, sodium tripolyphosphate, oxalic acid, phosphoric acid, sulfamic acid, and carboxymethyl inulin.

In other embodiments, the composition may comprise at least one chelating agent. Suitable chelating agents include but are not limited to EDTA, disodium EDTA, DTPA, HEDP, HEDTA, NTA, HEIDA, PBTC, phosphonates, carboxymethyl inulin, trisodium phosphate, sodium hexametaphosphate, sodium tripolyphosphate, tetrasodium pyrophosphate, potassium tripolyphosphate, tetrapotassium pyrophosphate, citric acid, gluconic acid, sodium gluconate, DTPMP, and combinations thereof.

In further embodiments, the composition may comprise at least one water softening agent. Non-limiting examples of suitable water softening agents include sodium triphosphate, sodium tripolyphosphate, sodium carbonate, sodium silicate, zeolites, and citric acid.

In some embodiments, the composition may comprise at least one foam control agent, such as ethylene oxide/propylene oxide copolymers or a silicone-based polymer such as dimethicone.

In still other embodiments, the composition may comprise at least one dispersant. Suitable dispersants include without limit phosphonates, carboxymethyl inulin, sodium hexametaphosphate, sodium tripolyphosphate, tetrasodium pyrophosphate, potassium tripolyphosphate, acrylic polymers, and combinations thereof.

In other embodiments, the composition may comprise at least one hydrotrope. Hydrotropes are compounds that improve the solubility of surfactants in aqueous solutions. Non-limiting examples of suitable hydrotropes include sodium toluenesulfonate, potassium toluene sulfonate, sodium xylene sulfonate, potassium xylene sulfonate, ammonium xylene sulfonate, sodium cumene sulfonate, ammonium cumene sulfonate, alkyl glucoside, complex coco imino glycinate, complex coco imino dipropionate, octyl imino dipropionate, phosphate ester potassium salt, and quaternary fatty methyl amine ethoxylate.

In yet alternate embodiments, the composition may comprise at least one linker. Linkers are amphiphiles that are used to increase surfactant-water interactions (i.e., hydrophilic linkers) or surfactant-oil interactions (i.e., lipophilic linkers). Suitable hydrophilic linkers include without limit alkyl naphthalene sulfonates such as mono- or di-methyl naphthalene sulfonate and diisopropyl naphthalene sulfonate. Non-limiting examples of suitable lipophilic linkers include hydrocarbyl alcohols having 8 or more carbon atoms in the principal chain or their low ethoxylated derivatives.

In other embodiments, the composition may comprise at least one filler. Non-limiting examples of suitable fillers include cellulose, methylcellulose, carboxymethylcellulose, microcrystalline cellulose, calcium sulfate, calcium carbonate, magnesium carbonate, dibasic calcium phosphate, magnesium carbonate, magnesium oxide, calcium silicate, sodium chloride, talc, modified starches, lactose, sucrose, mannitol, sorbitol, and combinations thereof.

In still other embodiments, the composition may comprise at least one disintegrant. Suitable disintegrants include without limit starches such as corn starch, potato starch, pregelatinized and modified starches thereof, sweeteners, clays, such as bentonite, microcrystalline cellulose, alginates, sodium starch glycolate, gums such as agar, guar, locust bean, karaya, pecitin, and tragacanth, and combinations thereof. Disintegrants that help other ingredients dissolve in solvents include Ceteths, which are prepared by reacting ethylene oxide with cetyl alcohol.

In some embodiments, the composition may comprise a solvent. The solvent may be a diluting solvent such as water or an aqueous solvent, or the solvent may be a polar solvent such as a glycol (such as propylene glycol, polyethylene glycols), glycerine, glycerides, diols, and the like.

In alternate embodiments, the composition may comprise skin conditioning agents. Suitable skin conditioning agents include glycerin, oils such as hydrogenated palm oil, coconut oil, lanolin, mineral oil, wheat germ oil, essential oils, liquid paraffin, botanical or herbal extracts, and proteins such as hydrolyzed collage, hydrolyzed oats, hydrolyzed soy protein, silk amino acids, and the like. The composition may also include salicylic acid, urea, alpha-hydroxy acids, and so forth.

In other embodiments, the composition may comprise at least one preservative. Non-limiting examples of suitable preservatives include antioxidants, such as alpha-tocopherol or ascorbate, and antimicrobials, such as parabens, chlorobutanol, phenol, glutaraldehyde, benzoic acid, quaternary ammonium salts, bronopol, hydrogen peroxide, sodium dichloroisocyanurate, sodium hypochlorite, and combinations thereof.

In still other embodiments, the composition may comprise at least one coloring agent. Suitable coloring agents include, but are not limited to, food, drug and cosmetic colors (FD&C), drug and cosmetic colors (D&C), external drug and cosmetic colors (Ext. D&C), and other dyes known in the industry.

In further embodiments, the composition may comprise at least one fragrance (or perfume) agent. Suitable fragrance (or perfume) agents are well known in the art.

The weight fraction of the additional agent(s) in the composition may be about 99% or less, about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

In various embodiments, the composition may be a liquid solution, an aqueous solution, an emulsion, a gel, a paste, a powder, a granular mixture, a pelleted mixture, or a solid.

(III) Methods for Using the Compounds of Formula (Ib)

A further aspect of the disclosure provides methods of using the compounds of Formula (Ib). In some embodiments, compounds of Formula (Ib) may be used as detergents or emulsifying agents in household or industrial laundry products, hard surface cleaning products, and other types of cleaning products. In other embodiments, compounds of Formula (Ib) may be used as cleaning agents in health and personal care products or cosmetic products. In still other embodiments, compounds of Formula (Ib) may be used as surfactants, emulsifying agents, or lubricants in pet or livestock feed or feed ingredients. In yet other embodiments, compounds of Formula (Ib) may be used as wetting agents in agricultural applications (e.g., pesticide or herbicide applications), textile industry applications (e.g., dry cleaning applications), or construction applications (e.g., road making operations). In further embodiments, compounds of Formula (Ib) may be used as foaming agents in ore mining operations, drilling operations, waste treatment applications, or fire-fighting applications. In yet other embodiments, compounds of Formula (Ib) may be used as emulsifying agents in petroleum production, oil cleanup procedures, mining operations, and other industries. In still other embodiments, compounds of Formula (Ib) may be used as demulsifying agents in chemical process industry. In yet further embodiments, compounds of Formula (Ib) may be used as surfactants in oil recovery, oil drilling or crude oil refining applications, metal processing industries, wood processing industries, or soil remediation.

In specific embodiments, a method for cleaning an article is provided. The method comprises contacting the article with a composition as described above in section (II). In some embodiments, the process may further comprise contacting the article with a solvent to remove the composition. Typically, the solvent will be an aqueous solvent such as water.

In certain embodiments, the article may be an inanimate object. Non-limiting examples of suitable inanimate objects include as laundry items such as clothing, uniforms, sheets, towels, and other linens; dishes, flatware, and cookware items; food preparation equipment; hard surfaces such as counters, floors, windows, sinks, and bathroom appliances; hospital and health care items; and industrial items or surfaces. As an example, the surface may be an oil contaminated surface, wherein the process entails removing the oil from the contaminated surface. In other embodiments, the article may be an animate object or a part of an animate object. Examples of suitable animate objects include but are not limited to hair, face, hands, feet, and other body parts.

(IV) Processes for the Preparation of Compounds of Formula (I)

Still another aspect of the present disclosure encompasses processes for the preparation of compounds of Formula (I), i.e., compounds of Formulas (Ia) and (Ib). Persons skilled in the art understand that a variety of different processes may be used to prepare the compounds disclosed herein. Exemplary processes are described below.

(a) Preparation of Compounds of Formula (Ia)

The process comprises an esterification reaction, and an optional oxidation reaction. In embodiments in which the oxidation reaction is performed, the oxidation reaction may occur before or after the esterification reaction. In instances in which the oxidation reaction occurs prior to the esterification reaction, the hydroxyl groups may be protected via the addition of a protecting group. Suitable protecting groups and means for attaching them are well known in the art. For example, see "Greene's Protective Groups in Organic Synthesis," 4th Ed. by P.G.M. Wuts and T.W. Greene, John Wiley & Sons, Inc., 2007.

(i) Esterification Reaction

The process comprises contacting compounds of Formula (II) with an acyl halide, $R^2C(O)X$, to form compounds of Formula (Ia) according to the following reaction scheme:

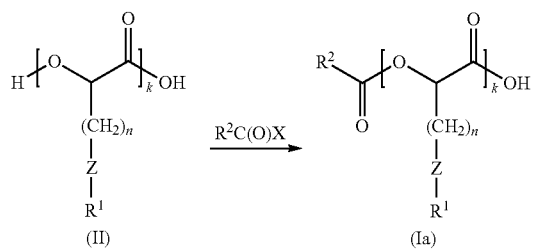

wherein $R^1$, $R^2$, Z, k, and n are as defined above in section (I), and X is a halide ion.

The identity of the acyl halide can and will vary. As detailed above in section (I), in specific embodiments, $R^2$ may be unsubstituted or substituted $C_{10}$ to $C_{30}$ alkyl or $C_8$ to $C_{30}$ alkenyl. Alkyl or alkenyl groups may be linear, branched, or cyclic, and alkenyl groups may contain from one to six carbon-carbon double bonds. In some embodiments, $R^2$ may be $C_{10}$ to $C_{24}$ alkyl or $C_8$ to $C_{24}$ alkenyl. In other embodiments, $R^2$ may be $C_{11}$, $C_{13}$, $C_{15}$, $C_{17}$, $C_{19}$, $C_{21}$, or $C_{23}$ alkyl or alkenyl. Moreover, the halide X may be chloride, bromide, fluoride, or iodide. The acyl halide may be derived from a natural fatty acid (the natural fatty acid may be linear, branched, saturated, or unsaturated). Non-limiting examples of suitable acyl halides include undecanoyl halide, dodecanoyl (lauroyl) halide, tridecanoyl halide, tetradecanoyl (myristoyl) halide, pentadecanoyl halide, hexadecanoyl (palmitoyl) halide, heptadecanoyl halide, octadecanoyl (stearoyl) halide, nonadecyoyl halide, arachidoyl halide, behenoyl halide, lignoceroyl halide, crotoyl halide, myristoloyl halide, palmitoloyl halide, sapienoyl halide, oloyl halide, elaidoyl halide, vaccenoyl halide, linoloyl halide, linoelaidoyl halide, linolenoyl halide, arachidonoyl halide, eicosapentaenoyl halide, erucoyl halide, and docosahexaenoyl halide.

The amount of acyl halide that is contacted with the compounds of Formula (II) can and will vary. In general, the mole-to-mole ratio of the compounds having Formula (II) to the acyl halide, $R^2C(O)X$, may range from about 1:0.2 to about 1:2. In some embodiments, the mole-to-mole ratio of the compounds of Formula (II) to the acyl halide may range from about 1:0.2 to about 1:0.5, from about 1:0.5 to about 1:1, from about 1:1 to about 1:1.5, or from about 1:1.5 to about 1:2. In a specific embodiment, the mole-to-mole ratio of the compounds having Formula (II) to the acyl halide may be about 1:0.5. In another specific embodiment, the mole-to-mole ratio of the compounds having Formula (II) to the acyl halide may be about 1:1.

Contact between the compounds of Formula (II) and the acyl halide may be conducted in the presence of a catalyst and a proton acceptor. In specific embodiments, the catalyst is a nucleophilic catalyst. Non-limiting examples of suitable nucleophilic catalysts include 4-dimethylaminopyridine (DMAP), pyridine or derivatives thereof, imidazole or derivatives thereof, amidines, isothioureas, and guanidines. In a specific embodiment, the nucleophilic catalyst may be DMAP. Typically, a catalytic amount of the catalyst is used in the process.

Suitable proton acceptors include, without limit, organic bases such as triethylamine, diisopropylethylamine, N-methylmorpholine, and mixtures thereof; organic buffers (for example, 4-(2-hydroxyethyl)piperazine-1-ethanesulfonic acid (HEPES), 2 (4 morpholinyl) ethanesulfonic acid (MES), 4-morpholinepropanesulfonic acid (MOPS), 1,4-piperazinediethanesulfonic acid (PIPES), salts and/or mixtures thereof); borate salts; di- and tri-basic phosphate salts; bicarbonate salts; hydroxide salts; carbonate salts, or mixtures thereof. In general, the mole-to-mole ratio of the compounds of Formula (I) to the proton acceptor ranges from about 1:0.1 to about 1:10. In various embodiments, the mole-to-mole ratio of the compounds of Formula (I) to the proton acceptor may range from range from about 1:0.5 to about 1:5, from about 1:1 to about 1:4, or from about 1:1.8 to about 1:2.2.

The reaction may be conducted in the presence of a solvent. The solvent may be a nonpolar solvent, a protic polar solvent, an aprotic polar solvent, or a combination thereof. Non-limiting examples of suitable nonpolar solvents include benzene, butyl acetate, tert-butyl methyl ether, chlorobenzene, chloroform, chloromethane, cyclohexane, dichlorobenzene, dichloromethane (DCM), dichloroethane, di-tert-butyl ether, dimethyl ether, diethylene glycol, diethyl ether, diglyme, diisopropyl ether, ethyl tert-butyl ether, ethylene oxide, fluorobenzene, heptane, hexane, methyl tert-butyl ether, toluene, and combinations thereof. Suitable protic polar solvents include without limit amides such as formamide, acetamide, and the like. Non-limiting examples of suitable aprotic polar solvents include acetone, acetonitrile, diethoxymethane, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl) ether, N,N-dimethylacetamide (DMAC), N-methyl-2-pyrrolidinone (NMP), 1,4-dioxane, ethyl acetate, ethyl formate, formamide, hexachloroacetone, hexamethylphosphoramide, methyl acetate, N-methylacetamide, methylethyl ketone, methylisobutyl ketone, N-methylformamide, methylene chloride, methoxyethane, morpholine, nitrobenzene, nitromethane, propionitrile, propyl acetates, sulfolane, tetramethylurea, tetrahydrofuran (THF), 2-methyl tetrahydrofuran, tetrahydropyran, trichloromethane, and combinations thereof. In specific embodiments, the solvent may be dichloromethane (DCM).

The volume-to-mass ratio (mL to g) of the solvent to the compounds of Formula (II) can and will vary. Typically, the volume-to-mass ratio of the solvent to the compounds of Formula (II) may range from about 1:1 to about 100:1. In various embodiments, the volume-to-mass ratio of the solvent to the compounds of Formula (II) may range from about 1:1 to about 3:1, from about 3:1 to about 10:1, from about 10:1 to about 30:1, or from about 30:1 to about 100:1. In preferred embodiments, the volume-to-mass ratio of the solvent to the compounds of Formula (II) may range from about 10:1 to about 30:1.

The reaction may be conducted at a temperature that ranges from about −10° C. to about 50° C. In certain embodiments, the temperature of the reaction may range from about 0° C. to about 10° C., from about 10° C. to about 20° C., from about 20° C. to about 30° C., from about 30° C. to about 40° C., or greater than about 40° C. In specific embodiments, the reaction may be initiated at about 0° C. and then the temperature may be increased to about room temperature. In general, the reaction will be conducted at atmospheric pressure.

The duration of the reaction can and will vary. In general, the reaction may be allowed to proceed from about 1 hour to about 24 hours or more. In some embodiments, the reaction may be allowed to proceed overnight (or from about 12 to about 18 hours). Typically, however, the reaction is allowed to proceed for a sufficient period of time until the reaction has proceeded to the desired degree of completion, as determined by means well known to those of skill in the art. In embodiments in which the reaction is allowed to go to completion, a "completed reaction" generally means that the final reaction mixture contains a significantly diminished amount of the compounds comprising Formula (II) and a significantly increased amount of the ester compounds comprising Formula (Ia) compared to the amounts of each present at the beginning of the reaction.

The compounds of Formula (Ia) may be isolated from the reaction mixture by means known in the art. Suitable means include extracting, washing, precipitating, filtering, distilling, evaporating, drying, chromatography, and combinations thereof. In some embodiments, individual monomers, dimers, etc. may be isolated. For example, compounds in which k varies can be separated via column chromatography.

The yield of the compounds of Formula (Ia) can and will vary. In general, the yield of the compound may be at least about 20%, at least about 30%, at least about 40%, at least about 50%, at least about 60%, at least about 70%, at least about 80%, or at least about 90%.

(ii) Optional Oxidation Reaction

In embodiments in which Z is sulfur, compounds comprising either Formula (II) or Formula (Ia) may be contacted with an oxidizing agent to convert the sulfur to a sulfoxide (or a sulfone). A variety of oxidizing agents may be used for this reaction. Non-limiting examples of suitable oxidizing agents include peroxy acids (e.g., meta-chloroperoxybenzoic acid (m-CPBA), peracetic acid, peroxysulfuric acid), hydrogen peroxide, perchlorates, chlorite, hypochlorite, chlorate, sulfuric acid, persulfuric acid, hexavalent chromium compounds, permanganate compounds, sodium perborate, nitric acids, nitrate compounds, metal oxidants (such as, e.g., benezeneselenic acid, lead tetraacetate, osmium tetroxide, phosphomolybdic acid hydrate, pyridinium chlorochromate, pyridinium dichromate, quinolinium dichromate, and the like). and combinations thereof. In specific embodiments, the oxidizing agent may be hydrogen peroxide or m-CPBA.

The mole-to-mole ratio of the sulfide containing compounds to the oxidizing agent can and will vary. In general, the mole-to-mole ratio of the sulfide compounds to the oxidizing agent may range from about 1:0.1 to about 1:20. In some embodiments, the mole-to-mole ratio of the sulfide compounds to the oxidizing agent may range from about 1:0.5 to about 1:5. In various embodiments, the mole-to-mole ratio of the sulfide compounds to the oxidizing agent may be about 1:1.0, 1:1.5, 1:2.0, 1:2.4, 1:2.6, 1:2.8, 1:3.0, 1:3.2, 1:3.6, or 1:4.0. In exemplary embodiments, the mole-to-mole ratio of the sulfide compounds to the oxidizing agent may be about 1:1 or about 1:3.

The oxidation reaction may be performed in the presence of a solvent. The solvent may be a nonpolar solvent, a protic solvent, an aprotic solvent, or a combination thereof, depending upon the reactants. Suitable solvents and ratios are listed above.

The oxidation reaction may be conducted at a temperature that ranges from about −10° C. to about 50° C. In certain embodiments, the temperature of the reaction may be about 0° C., 10° C., 20° C., 25° C., or 30° C. In one embodiment, the reaction may be allowed to proceed at about 0° C. In another embodiment, the reaction may be allowed to proceed for a first period of time at 0° C. and a second period of time at room temperature. In still another embodiment, the reaction may be conducted at room temperature. Typically, the reaction will be conducted at atmospheric pressure.

The duration of the reaction can and will vary. In general, the reaction may be allowed to proceed from several hours to several days. Typically, however, the reaction may be allowed to proceed for a sufficient period of time until the reaction is complete or substantially complete, as determined by means well known to those of skill in the art. In this context, the final reaction mixture contains a significantly diminished amount of the sulfide compounds and a significantly increased amount of the oxidized compounds compared to the amounts of each present at the beginning of the reaction.

The sulfoxide (or sulfone) compounds may be isolated from the reactants in the reaction mixture by means well known in the art. Suitable means include extracting, washing, precipitating, filtering, distilling, evaporating, drying, chromatography, chiral chromatography, and combinations thereof.

The yield of the sulfoxide (or sulfone) compounds can and will vary. In general, the yield of the compounds may be at least about 20%, at least about 30%, at least about 40%, at least about 50%, at least about 60%, at least about 70%, at least about 80%, or at least about 90%.

(iii) Exemplary Process

An exemplary process entails an esterification reaction followed by an oxidation reaction. The process comprises contacting sulfide compounds of Formula (IIa) with the acyl halide, as detailed above in section (IV)(a)(i), to form acylated compounds of Formula (Ic), and the compound s of Formula (Ic) then are contacted with the oxidizing agent, as detailed above in section (IV)(a)(ii), to form the compounds of Formula (Ia), according to the following scheme:

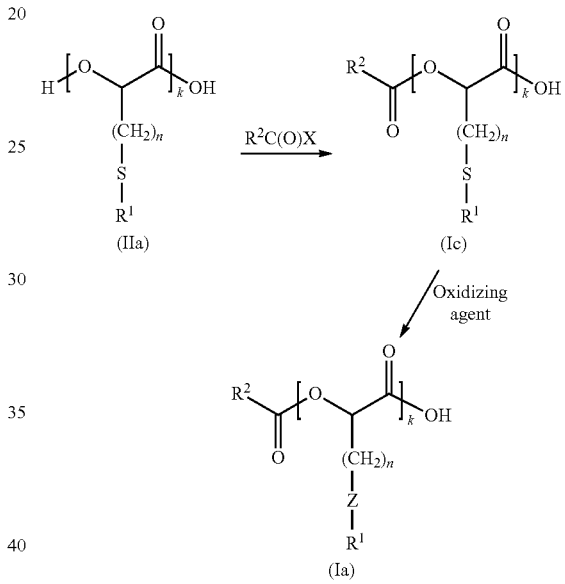

wherein $R^1$, $R^2$, X, Z, k, and n are as defined above.

(b) Preparation of Compounds of Formula (Ib)

The process comprises contacting the compounds of Formula (Ia) with a salt, MA, to form the compounds of Formula (Ib) according to the following reaction scheme:

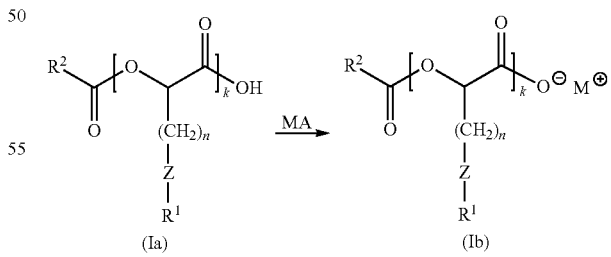

wherein $R^1$, $R^2$, Z, M, k, and n are as defined above in section (I), and A is an anion.

The salt comprises a cation, M, as described above in section (I), and an anion A. Suitable anions include, without limit, hydroxide, hydride, acetate, amide, carbonate, hydrogen carbonate, bromide, bromate, chloride, chlorate, chlorite, hypochlorite, chromate, dichromate, formate, nitrite, nitride, nitrite, perchlorate, peroxide, phosphate, hydrogen phosphate, dihydrogen phosphate, permanganate, oxide, oxalate, sulfate, sulfite, hydrogen sulfate, sulfide, thiosulfate, and thiocyanate. In some embodiments, the salt is free (e.g., is in solution). In other embodiments, the salt is bound to a resin (e.g., an ion exchange resin). In specific embodiments, the salt may be sodium hydroxide, potassium hydroxide, sodium bicarbonate, potassium bicarbonate, and the like.

The amount of salt contacted with the compounds of Formula (Ia) can and will vary. In general, the mole-to-mole ratio of the compounds of Formula (Ia) to the salt may range from about 1:0.5 to about 1:2. In specific embodiments, the mole-to-mole ratio of the compounds of Formula (Ia) to the salt may be about 1:1.

The reaction may be performed in the presence of a solvent. Suitable solvents and ratios are detailed above in section (IV)(a)(i). The reaction may proceed under homogenous or heterogeneous reaction conditions. The temperature of the reaction may vary, but generally ranges from about 15° C. to about 35° C. The duration of the reaction may vary, but generally ranges from about one hour to about one day. In general, the reaction is allowed to proceed until the reaction is complete or substantially complete, as determined by means well known to those of skill in the art.

The compounds of Formula (Ib) may be isolated from the reaction mixture by means known in the art. Suitable means include extracting, washing, precipitating, filtering, distilling, evaporating, drying, chromatography, and combinations thereof.

The yield of the compounds of Formula (Ib) can and will vary. In general, the yield of the compounds may be at least about 20%, at least about 30%, at least about 40%, at least about 50%, at least about 60%, at least about 70%, at least about 80%, or at least about 90%.

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The term "acyl," as used herein alone or as part of another group, denotes the moiety formed by removal of the hydroxyl group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes saturated hydrocarbyl groups that contain from 1 to 30 carbon atoms. They may be linear, branched, or cyclic, may be substituted as defined below, and include methyl, ethyl, propyl, isopropyl, butyl, hexyl, heptyl, octyl, nonyl, and the like.

The term "alkenyl" as used herein describes hydrocarbyl groups which contain at least one carbon-carbon double bond and contain from 1 to 30 carbon atoms. They may be linear, branched, or cyclic, may be substituted as defined below, and include ethenyl, propenyl, isopropenyl, butenyl, isobutenyl, hexenyl, and the like.

The term "alkoxide" or "alkoxy" as used herein is the conjugate base of an alcohol. The alcohol may be straight chain, branched, cyclic, and includes aryloxy compounds.

The term "alkynyl" as used herein describes hydrocarbyl groups which contain at least one carbon-carbon triple bond and contain from 1 to 30 carbon atoms. They may be linear or branched, may be substituted as defined below, and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The term "aryl" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

A "detergent" is a water-soluble "cleaning agent" that has wetting-agent and emulsifying-agent properties.

The terms "demulsifying agent" or "demulsifier" refers to a compound that facilitates the separation of emulsions.

As used herein, the terms "emulsifying agent" or "emulsifier" refer to a compound that is soluble in both oil and water and enables oil to be uniformly dispersed in water as an emulsion.

A "foaming agent" is a substance that facilitates the formation of foam.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. They may be straight, branched, or cyclic. Unless otherwise indicated, these moieties preferably comprise 1 to 20 carbon atoms.

A "lubricant" is a substance that is used to reduce friction and prevent sticking during manufacturing processes.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

As used herein, the term "surfactant" refers to a compound that lowers the surface tension of a liquid in which it is dissolved.

A "wetting agent" is a compound that lowers the surface tension of a liquid and promotes the spreading of the liquid on a surface or the penetration of the liquid into a material.

Having described the invention in detail, it will be apparent that modifications and variations are possible without departing from the scope of the invention defined in the appended claims.

EXAMPLES

The following examples illustrate various embodiments of the invention.

Example 1

Synthesis of
4-(methylsulfinyl)-2-(palmitoyloxy)butanoic acid
($C_{16}$ESOCOOH)

Step 1: Synthesis of 4-(methylthio)-2-(palmitoyloxy)butanoic acid. To 2-hydroxy-4-(methylthio)butanoic acid (10.08 g, 67.1 mmol) in dichloromethane (DCM; 200 mL) at 0° C. was added 4-dimethylaminopyridine (DMAP; cat.), triethylamine ($Et_3N$; 18.7 mL, 134 mmol) followed by palmitoyl chloride (10.2 mL, 33.6 mmol) dropwise over about 1 hour. The reaction was allowed to warm to room temperature with stirring overnight. The solution was concentrated to a small volume and re-dissolved in heptane (300 mL). The organic layer was washed with 1N HCl (3×100 mL), water (2×100 mL) and brine (1×100 mL), then dried over magnesium sulfate, filtered and evaporated to give 14.4 g of a white solid. A portion (7 g) of this solid was purified by silica gel chromatography with 0-25% ethyl acetate (EA)/heptane and 1% acetic acid (AcOH) additive to give a white solid (5.8 g, 45%).

Step 2: Synthesis of 4-(methylsulfinyl)-2-(palmitoyloxy)butanoic acid. To a solution of 4-(methylthio)-2-(palmitoyloxy)butanoic acid (5.8 g, 14.9 mmol) in methanol (30 mL) at 0° C. was added hydrogen peroxide (30%, 4.57 mL, 44.8 mmol). The reaction was warmed to room temperature and was stirred for ~5.5 hours. The reaction was diluted with 200 mL of DCM and washed with water (1×100 mL). An emulsion formed which was allowed to separate overnight. The organic layer was washed with 10% sodium bisulfite (1×100 mL), dried over magnesium sulfate, filtered and evaporated to give a white solid. The solid was purified by silica gel chromatography with 2-10% MeOH/DCM containing 1% AcOH additive to give a white solid (4.38 g, 73%). $^1$H NMR (500 MHz, DMSO-$d_6$) δ ppm 0.85 (3H) 1.09-1.35 (24H) 1.44-1.61 (2H) 2.01-2.25 (2H) 2.29-2.40 (2H) 2.54 (3H) 2.62-2.94 (2H) 4.96 (1H) 13.06-13.36 (1H). m/z 405 (MH$^+$)

Example 2

Synthesis of
4-(methylthio)-2-(dodecanoyloxy)butanoic acid
($C_{12}$ESCOOH)

Synthesis of 4-(methylthio)-2-(dodecanoyloxy)butanoic acid ($C_{12}$ESCOOH). Prepared in a similar manner as $C_{16}$ESCOOH described in step 1 of Example 1, except lauroyl chloride was used as the acylating agent, to give a white solid (1.22 g, 11%). $^1$H NMR (500 MHz, DMSO-$d_6$) δ ppm 0.85 (3 H) 1.16-1.32 (16 H) 1.52 (2 H) 1.93-2.02 (2 H) 2.04 (3 H) 2.34 (2 H) 2.53 (2 H) 4.90-4.97 (1 H) 13.11 (1H). m/z 355 (MNa$^+$)

Example 3

Synthesis of
4-(methylsulfinyl)-2-(dodecanoyloxy)butanoic acid
($C_{12}$ESOCOOH)

Step 1: Synthesis of methyl 2-hydroxy-4-(methylsulfinyl)butanoate. To a solution of methyl 2-hydroxy-4-(methylthio)butanoate (5.10 g, 31.1 mmol) in DCM (150 mL) at 0° C. was added meta-chloroperoxybenzoic acid (m-CPBA; 77%, 6.90 g, 30.8 mmol) portion-wise over 30 min. The resulting mixture was allowed to warm to room temperature with stirring for two days. The mixture was treated with water (100 mL), stirred overnight, and filtered. The filtrate was extracted with water (2×100 mL, 3×50 mL) and the combined aqueous layers were evaporated to give an oil. The oil dissolved in EA was dried over magnesium sulfate, filtered and evaporated. Purification by silica gel chromatography with 0-7% methanol/DCM followed by elution through a Si-Carbonate resin column with methanol gave a colorless oil (4.29 g, 77%).

Step 2: Synthesis of 2-hydroxy-4-(methylsulfinyl)butanoic acid. A solution of methyl 2-hydroxy-4-(methylsulfinyl)butanoate (3.12 g, 31.1 mmol) in 1N HCl (50 mL) was heated at 60° C. for 6.5 hrs. The solution was concentrated by rotary evaporation and dried on the high vacuum to give a light yellow oil (3.44 g, quant.).

Step 3: Synthesis of 2-(dodecanoyloxy)-4-(methylsulfinyl)butanoic acid. To a solution of 2-hydroxy-4-(methylsulfinyl)butanoic acid (3.19 g, 19.2 mmol) in DCM (40 mL) at 0° C. was added DMAP (cat.) and $Et_3N$ (5.35 mL, 38.4 mmol) followed by lauroyl chloride (4.44 mL, 19.2 mmol) dropwise over 1.5 hrs. The reaction was warmed to room temperature and stirred until judged complete by HPLC analysis. The reaction was concentrated to a small volume, re-dissolved in EA (100 mL) and washed with 1 N HCl (3×100 mL), brine (1×100 mL), dried over magnesium sulfate, filtered and evaporated to give a solid. The solid was purified by silica gel chromatography with 0-10% methanol/DCM with 1% AcOH additive to give a white solid (2.78 g, 42%). $^1$H NMR (500 MHz, DMSO-d$_6$) δ ppm 0.86 (3 H) 1.25 (16 H) 1.48-1.61 (2 H) 2.02-2.25 (2 H) 2.30-2.42 (2 H) 2.56 (3 H) 2.62-2.93 (2 H) 4.97 (1 H). m/z 349 (MH$^+$).

Example 4

Preparation of the Sodium Carboxylate Salts

Dowex MAC-3 resin (proton form) was swollen and neutralized with excess NaOH/water solution, and then assembled into a column. After the resin was balanced with 2 column volumes of 30 vol % water in ethanol, 1 column volume of a 0.1 g/mL acid in 30 vol % water in ethanol solution was loaded and incubated in the column for 10 min. Subsequently, the resin was rinsed with 2 column volumes of 30 vol % water in ethanol, and the eluent was collected. The pH of the 1 wt % solutions/suspensions of the solids increased from 4 to 8 after passing through the column. The solvent was then evaporated under vacuum at mild heat (40° C.) to provide the sodium carboxylate salts. The sodium salts were fully soluble in water (deionized with 18MΩ resistivity), while the starting carboxylic acids were insoluble.

Example 5

Water Solubility and Surface Chemical Properties of the Sulfoxide/Sulfide Carboxylates Surfactant properties of the sulfoxide/sulfide carboxylates prepared above were investigated and compared to commercially available anionic surfactants such as the linear carboxylates, sodium laurate (NaL), sodium dodecyl sulfate (SDS), and sodium dodecylbenzene sulfonate (SDBS).

The solubility of the surfactants in water was assessed visually at room temperature. The mixture at each concentration was examined after at least 10 min of mild shaking and ultrasonic bath agitation to see if the surfactant completely dissolved. Solutions were observed for two hours after mixing to ascertain the presence of supersaturation. Surface tension was determined with a Wilhelmy Plate tensiometer (Cahn DCA-322) at room temperature. Glass slides manufactured by Corning with a width of 22 mm and thickness of 0.1 mm were used as probes. The motor speed was set to be 100 μm/sec. The CMC was determined from the break point of Yvs. log C diagram with a custom Microsoft Visual Basic program. The results presented in Table 1.

TABLE 1

Water solubility and surface chemical properties of sulfoxide/sulfide carboxylate surfactants with comparisons

| Surfactants | Water Solubility (mM) | CMC (mM) | Y$_{CMC}$ (mN/m) | pC20 | CMC/ C20 |
|---|---|---|---|---|---|
| C$_{12}$ESCOONa | 282 | 1.0 | 35 | 3.84 | 5.55 |
| C$_{12}$ESOCOONa | >1000 | 1.7 | 40 | 3.27 | 3.15 |
| C$_{16}$ESOCOONa | 117 | 0.54 | 42 | 4.07 | 4.56 |
| C$_{12}$H$_{25}$C$_6$H$_4$SO$_3^-$Na$^+$ (SDBS) | 575$^a$ | 3.1 | 34 | 3.24 | 5.30 |
| C$_{11}$H$_{23}$COO$^-$Na$^+$ (NaL) | 90 | 19.1 | 30 | 3.32 | 38.5$^b$ |
| C$_{12}$H$_{25}$SO$_4^-$Na$^+$ (SDS) | 350$^c$ | 12.4$^d$ | 40$^d$ | 2.36$^d$ | 2.6$^d$ |

$^a$See Acevedo et al., Energy & Fuels, 2005, 19: 1548-1560.
$^b$See Jackson et al., Journal of Surfactants and Detergents, 2013, 16: 893-902.
$^c$See Guzman et al., Petroleum Science and Technology, 2009, 27: 801-816.
$^d$See Dahanayake et al., Journal of Physical Chemistry, 1986, 90: 2413-2418.

The CMCs of the sulfoxide/sulfide carboxylates are lower than those of SDS, SDBS, and NaL (measured at the same temperature). The comparison between C$_{12}$ESCOONa and C$_{12}$ESOCOONa represents the difference between sulfide and sulfoxide functional groups. Sulfur oxidation increased the water solubility and CMC, as expected. The sulfoxide/sulfide carboxylates had relatively high pC20 values, indicating high efficiency in lowering the surface tension, even though their surface tensions at the CMC and surface excess concentrations were not superior to other anionic surfactants, suggesting comparable effectiveness of surface adsorption. One important parameter is CMC/C20, which is an indicator of the tendency of liquid-air adsorption versus micelle formation (the higher the value, the more favored is surface adsorption). A possible reason that the sulfoxide/sulfide carboxylate surfactants favor micelle formation more than the other surfactants is that the sulfoxide/sulfide carboxylates have a smaller packing factor than the straight-chain hydrophobes.

Example 6

Precipitation Tendencies of the Sulfoxide/Sulfide Carboxylates

The Krafft temperature of the surfactant with the concentration at the room temperature CMC was determined by cooling the solution to 4° C. and then raising the temperature by 1° C. steps and visually inspecting its phase behavior after the solution reached thermal equilibrium. For hardness tolerance, a known amount of calcium chloride was added to the solution prior to cooling to 4° C. The solution was then heated to 25° C. and the solubility was assessed visually. The results are presented in Table 2.

TABLE 2

Krafft point and calcium tolerance of sulfoxide/sulfide carboxylate surfactants with comparisons

| Surfactants | Krafft Point (° C.) | CaCl$_2$ Tolerance (μM) | Hardness Tolerance (ppm as CaCO$_3$) |
|---|---|---|---|
| C$_{12}$ESCOONa | <4 | 100 | 10 |
| C$_{12}$ESOCOONa | <4 | 5000 | 500 |
| C$_{16}$ESOCOONa | <4 | 100 | 10 |
| NaL | 13$^a$ | 0.5 | 0.05 |
| SDS | 15$^b$ | 40$^c$ | 4$^c$ |

$^a$See Blanco et al., Journal of Colloid and Interface Science, 2005, 288: 247-260.
$^b$See Glukhareva et al., Colloid Journal, 1995, 57: 253-255.
$^c$See Stellner et al., Langmuir, 1989, 5: 70-77.

Within 48 hours, 1 wt % solutions of $C_{12}ESCOONa$, $C_{12}ESOCOONa$ and $C_{16}ESOCOONa$ did not show precipitation in the 4° C. water bath, and hence the Krafft points of all three sulfoxide/sulfide carboxylate surfactants are lower than 4° C. Based on the reported data, the sulfoxide/sulfide carboxylate surfactants have better low temperature operability than SDS (Krafft point at 15° C.). In terms of hardness tolerance, the $C_{12}ESCOONa$ solution showed precipitation with $CaCl_2$ only above 100 µM. NaL and SDS were also tested; the results show that the $C_{12}ESCOONa$ had approximately 2.5 orders of magnitude better calcium tolerance than the linear carboxylate (which agrees with the water solubility data) and about half an order of magnitude better than the linear sulfate, SDS. This improved calcium tolerance is a combined effect of the increased hydrogen bonding due to the ester group, and the branching in the head group. Oxidation of the sulfur atom further improved its hardness tolerance. $C_{12}ESOCOONa$ has a hardness tolerance of 5000 mM of $CaCl_2$, which is 50 times higher than the unoxidized form. In fact, the increased hardness tolerance from sulfur oxidation is exactly offset by 4 additional hydrocarbon units, which is observed by comparing the data of $C_{12}ESCOONa$ and $C_{16}ESOCOONa$. Due to its good water solubility, low CMC and high hardness tolerance, $C_{12}ESOCOONa$ is a potential calcium tolerant anionic surfactant, and even a candidate as a builder in hard-water formulations.

Example 7

Wetting Ability of Sulfide Carboxylate

The Draves wetting test was performed according to ASTM D2281-68. 500 mL of surfactant solution was poured into a 500 mL graduated cylinder (38 cm in height), and a 5.0 g standard skein hooked with a lead anchor was dropped into the solution. The skein floats in the solution initially and sinks when wetted, and the time taken was recorded as the time of wetting. The data are presented in Table 3.

TABLE 3

Draves wetting test results of sulfide carboxylate with comparisons

| Surfactants | Draves wetting time (s) of 0.1 wt % solution |
|---|---|
| $C_{12}ESCOONa$ | 11 |
| NaL | 52 |
| SDS | 11 |

For the Draves wetting test, 0.1 wt % solutions were used for all the surfactants. $C_{12}ESCOONa$ outperformed NaL in wetting time with a comparable performance to SDS. $C_{12}ESCOONa$ is a larger molecule than NaL and SDS, and should have a smaller diffusion coefficient and hence a higher wetting time, but since $C_{12}ESCOONa$ has lower CMC, this surfactant should be less likely to experience monomer depletion in the Draves wetting test than the other two surfactants.

Example 8

Foaming Ability of Sulfide Carboxylate

The Ross-Miles foam test was performed according to the test protocol described in ASTM D1173-07. The surfactants tested were $C_{12}ESCOONa$, SDS, SDSB, and alkyl ether sulfate (AES). 50 mL of each surfactant solution (1 wt %) was carefully poured into the 1 meter glass column, without creating any foam, which is called the receiver. A 200 mL pipette with the surfactant solution is placed 90 cm above the receiver and the solution is allowed to drop into the foam receiver. The height of the foam produced is measured immediately and after 5 minutes.

$C_{12}ESCOONa$ generated foam heights comparable to the reference anionic surfactants, but dissipates much faster. Fast dissipation indicates lack of surface cohesiveness. Quick dissipation of foams is a desirable property in low-foaming applications, such as automatic dishwashing and laundry.

What is claimed is:

1. A compound of Formula (I):

$$R^2 \underset{O}{\overset{O}{\|}} -[O]_k- \underset{(CH_2)_n}{\overset{O}{\|}} -O-Y$$
$$\qquad\qquad\qquad\quad |$$
$$\qquad\qquad\qquad\quad Z$$
$$\qquad\qquad\qquad\quad |$$
$$\qquad\qquad\qquad\quad R^1$$

wherein:
   $R^1$ is $C_1$-$C_6$ alkyl;
   $R^2$ is $C_{10}$-$C_{30}$ alkyl or $C_8$-$C_{30}$ alkenyl;
   Y is a cation chosen from hydrogen, ammonium, alkali metal, alkaline earth metal, or transition metal;
   Z is sulfur, sulfoxide, or sulfone;
   k is an integer from 1 to 10; and
   n is an integer from 1 to 3.

2. The compound of claim 1, wherein Y is hydrogen, $R^1$ is methyl, Z is sulfur or sulfoxide, and n is 2.

3. The compound of claim 1, wherein Y is a cation other than hydrogen, $R^1$ is methyl, Z is sulfur or sulfoxide, and n is 2.

4. The compound of claim 3, wherein Y is an alkali metal.

5. The compound of claim 3, wherein the compound has surfactant properties.

6. The compound of claim 3, wherein the compound has a critical micelle concentration (CMC) in water at room temperature and atmospheric pressure.

7. The compound of claim 3, wherein the compound is used as a cleaning agent in health and personal care products or cosmetic products; a detergent or emulsifying agent in household or industrial laundry products or cleaning products; a surfactant, emulsifying agent, or lubricant in pet or livestock feed or feed ingredients; a wetting agent in agricultural applications, textile industry applications, or construction applications; a foaming agent in ore mining operations, drilling operations, waste treatment applications, or fire-fighting applications; an emulsifying agent in petroleum production, oil cleanup procedures, or mining operations; a demulsifying agent in chemical process industry; or a surfactant in oil recovery, oil drilling or crude oil refining applications, metal processing industries, wood processing industries, or soil remediation.

8. A mixture comprising two or more compounds of Formula (I) as defined in claim 1.

9. A detergent composition comprising at least one compound of Formula (I) as defined in claim 3.

10. The detergent composition of claim 9, further comprising an agent chosen from a pH regulating agent, an enzyme, a surfactant, an optical brightening agent, a bleaching agent, a thickening agent, a scale inhibitor, a chelating agent, a water softening agent, a foam control agent, a dispersant, a hydrotrope, a linker, a filler, a disintegrant, a solvent, a preservative, a coloring agent, a fragrance agent, or combinations thereof.

11. A mixture comprising two or more compounds of Formula (I) as defined in claim 2.

12. The mixture of claim 11, wherein the two or more compounds of Formula (I) are identical except that k varies from 1 to 10.

13. A mixture comprising two or more compounds of Formula (I) as defined in claim 3.

14. The mixture of claim 13, wherein the two or more compounds of Formula (I) are identical except that k varies from 1 to 10.

* * * * *